United States Patent
Bhattacharya

(10) Patent No.: US 8,287,719 B2
(45) Date of Patent: Oct. 16, 2012

(54) METHODS FOR THE DETECTION AND DIAGNOSIS OF MALARIA USING AN ELECTROCHEMICAL SENSOR

(75) Inventor: Jaydeep Bhattacharya, Kolkata (IN)

(73) Assignee: Empire Technology Development LLC, Wilmington, DE (US)

( * ) Notice: Subject to any disclaimer, the term of this patent is extended or adjusted under 35 U.S.C. 154(b) by 318 days.

(21) Appl. No.: 12/750,304

(22) Filed: Mar. 30, 2010

(65) Prior Publication Data

US 2011/0192731 A1 Aug. 11, 2011

(30) Foreign Application Priority Data

Feb. 9, 2010 (IN) .............................. 118/KOL/2010

(51) Int. Cl.
*G01F 1/64* (2006.01)
*G01N 27/26* (2006.01)
*G01N 17/00* (2006.01)

(52) U.S. Cl. ........................ 205/792; 205/777.5; 436/66
(58) Field of Classification Search .................. 205/792; 204/777.5, 403.01; 436/66

See application file for complete search history.

(56) References Cited

U.S. PATENT DOCUMENTS

2004/0099531 A1  5/2004  Srinivasan et al.

OTHER PUBLICATIONS

Abdollah Salimi, Ensiyeh Sharifi, Abdollah Noorbakhsh, Saied Soltanian, Direct voltammetry and electrocatalytic properties of hemoglobin immobilized on a glassy carbon electrode modified with nickel oxide nanoparticles, Electrochemistry Communications, vol. 8, Issue 9, Sep. 2006, pp. 1499-1508.*

Kit Mukesh K. Sharma, Vepa K. Rao, Gauri S. Agarwal, Ganga P. Rai, N. Gopalan, Shri Prakash, S. K. Sharma, and R. Vijayaraghava "Highly Sensitive Amperometric Immunosensor for Detection of *Plasmodium falciparum* Histidine-Rich Protein 2 in Serum of Humans with Malaria: Comparison with a Commercial" J. Clin. Microbiol. Nov. 2008 46:11 3759-3765.*

Takashi Yonetani, Sunglck Park, Antonio Tsuneshige, Kiyohiro Imai, and Kenji Kanaori "Global Allostery Model of Hemoglobin: Modulation of O2 Affinity, Cooperativity, and Bohr Effect by Heterotropic Allosteric Effectors" J. Biol. Chem. 2002 277: 34508-34520. First Published on Jul. 9, 2002.*

Rezaei-Zarchi S, Saboury A A, Ghourchian H, Hong J, Barzegar A, Norouzi P, Moosavi-Movahedi A A, Ganjali M R and Javed A "Electrochemical investigation of the effect of some organic phosphates on haemoglobin"; J. Biosci. 32 271-278, 2007.*

"Malaria: Parasite Biology, Pathogenesis, and Protection," Sherman, I. W., Ed.; ASM Press, Washington D.C., 1998.

Atha, D. et al., "Tetramer-Dimer Dissociation in Hemoglobin and the Bohr Effect," *The Journal of Biological Chemistry*, vol. 251, No. 18, Sep. 25, 1976, pp. 5537-5543.

Bunn, H. F., "Differences in the Interaction of 2,3-Diphosphoglycerate with Certain Mammalian Hemoglobins," *Science*, vol. 172, Jun. 4, 1971, pp. 1049-1050.

(Continued)

*Primary Examiner* — Jeffrey T Barton
*Assistant Examiner* — Louis Rufo
(74) *Attorney, Agent, or Firm* — Foley & Lardner LLP

(57) ABSTRACT

Disclosed are apparatuses for detecting hemoglobin in patient samples. The apparatuses include a primary electrode and a reference electrode. The apparatus is configured to measure current or voltage generated between the primary electrode and the reference electrode in response a redox reaction catalyzed by hemoglobin. The apparatuses can detect a variety of hemoglobins, including dimeric hemoglobin associated with malaria. Also disclosed are biosensor systems including the apparatuses and methods of using the biosensor systems.

19 Claims, 8 Drawing Sheets

OTHER PUBLICATIONS

Bunn, H. F. et al., "The Interaction of 2,3-Diphosphoglycerate with Various Human Hemoglobins," *The Journal of Clinical Investigation*, vol. 49, 1970, pp. 1088-1095.

Chen, Shihong et al., "Amperometric third-generation hydrogen peroxide biosensor based on the immobilization of hemoglobin on multiwall carbon nanotubes and gold colloidal nanoparticles," *Biosensors and Bioelectronics*, vol. 22, 2007, pp. 1268-1274.

Greenwood, B. et al., "Malaria in 2002," *Nature*, vol. 415, Feb. 7, 2002, pp. 670-672.

Griffon, N. et al., "Tetramer-dimer equilibrium of oxyhemoglobin mutants determined from auto-oxidation rates," *Protein Science*, vol. 7, 1998, pp. 673-680.

Hoffman, S. L. et al., "*Plasmodium*, human and *Anopheles* genomics and malaria," *Nature*, vol. 415, Feb. 7, 2002, pp. 702-709.

IP, S. H. C. et al., "Kinetics of Deoxyhemoglobin Subunit Dissociation Determined by Haptoglobin Binding: Estimation of the Equilibrium Constant from Forward and Reverse Rates," *Biochemistry*, vol. 15, No. 3, 1976, pp. 654-660.

Miller, L. H. et al., "The pathogenic basis of malaria," *Nature*, vol. 415, Feb. 7, 2002, pp. 673-679.

Richie, T. L. et al., "Progress and challenges for malaria vaccines," *Nature*, vol. 415, Feb. 7, 2002, pp. 694-701.

Rogers, D. J. et al., "Satellite imagery in the study and forecast of malaria," *Nature*, vol. 415, Feb. 7, 2002, pp. 710-715.

Sachs, J. et al., "The economic and social burden of malaria," *Nature*, vol. 415, Feb. 7, 2002, pp. 680-685.

Salimi, A. et al., "Direct voltammetry and electrocatalytic properties of hemoglobin immobilized on a glassy carbon electrode modified with nickel oxide nanoparticles," *Electrochemistry Communications*, vol. 8, 2006, pp. 1499-1508.

Tan, A. L. et al., "The Effect of Inositol Hexaphosphate on the Allosteric Properties of Carp Hemoglobin," *The Journal of Biological Chemistry*, vol. 248, No. 21, Nov. 10, 1973, pp. 7412-7416.

Ridley, Robert G., Medical need, scientific opportunity and the drive for antimalarial drugs, Nature, vol. 415, Feb. 7, 2002, pp. 686-693, (includes title page and table of contents).

\* cited by examiner

METHODS FOR THE DETECTION AND DIAGNOSIS OF MALARIA USING AN ELECTROCHEMICAL SENSOR

CROSS-REFERENCE TO RELATED APPLICATIONS

This application claims priority to India Patent Application No. 118/KOL/2010, filed Feb. 9, 2010, the entire contents of which are hereby incorporated by reference in its entirety.

TECHNICAL FIELD

The present technology relates generally to the fields of electrochemical cells and disease diagnosis, including the diagnosis of malaria.

BACKGROUND

The following description is provided to assist the understanding of the reader. None of the information provided or references cited is admitted to be prior art to the present invention.

Malaria is one of the major protozoan diseases and afflicts more than 500 million people (mostly in developing countries). Each year, malaria infections kill between one and two million people, most of whom are children. In humans, malaria is caused by four different protozoa species of the genus Plasmodium, with P. falciparum being the most lethal. The life cycle of the parasite is very complex and proceeds through several asexual and sexual stages (Malaria: Parasite Biology, Pathogenesis, and Protection; Sherman, I. W., Ed. ASM Press: Washington, D.C., 1998). Plasmodium sporozoites are transmitted by female Anopheles mosquitoes and are injected in the blood of a human host. The initial proliferation takes place in the liver and merozoites are formed which are released back into the blood stream. The parasite then invades red blood cells (RBCs) and matures, forming a ring-shaped cell. Within 24 h, the matured parasite enters the trophozoite stage where it catabolizes most of the RBC cytoplasm. Through the final (schizont) stage, the parasite undergoes several divisions to produce up to 32 new merozoites that burst the host RBC and invade new erythrocytes.

Chemical and biological sensors are devices that can detect or quantify analytes by virtue of interactions between targeted analytes and macromolecular binding agents such as, but not limited to, enzymes, receptors, heavy metal chelators, or antibodies. Chemical and biological sensors are commonly categorized according to two features, namely, the type of material utilized as binding agent and the means for detecting an interaction between binding agent and targeted analyte or analytes. Major classes of biosensors include enzyme (or catalytic) biosensors, immunosensors and DNA biosensors. Chemical sensors make use of synthetic macromolecules for detection of target analytes. Some common methods of detection are based on electron transfer, generation of chromophores, or fluorophores, changes in optical or acoustical properties, or alterations in electric properties when an electrical signal is applied to the sensing system. For example, upon interaction with an analyte, an enzyme may generate electrons, a colored chromophore or a change in pH (due to release of protons) as the result of the relevant catalytic enzymatic reaction. Alternatively, upon interaction with an analyte, an enzyme may cause a change in a fluorescent or chemiluminescent signal that can be recorded by an appropriate detection system.

SUMMARY

Provided herein are methods and apparatuses for the detection of hemoglobin, which may be useful for, inter alia, the diagnosis of malaria. Accordingly, in one aspect, the present disclosure provides a method for diagnosing malaria in a subject comprising: (a) introducing a test sample containing hemoglobin from the subject into a reaction cell including a primary electrode and a reference electrode; (b) adding hydrogen peroxide to the reaction cell; (c) measuring a current, voltage and/or resistance between the primary electrode and the reference electrode; and (d) comparing the level of the measured current, voltage and/or resistance of the test sample to a reference level, wherein a difference between the reference level and the level of the measured current, voltage and/or resistance indicates the presence of malaria in the subject.

In one embodiment, the electrodes are each independently made of or coated by a material selected from gold, platinum, palladium, silver, carbon, copper, iridium, cobalt, nickel, or indium tin oxide. In one embodiment, the primary electrode is made of or totally or partially coated with nickel. In an illustrative embodiment, the primary electrode is a platinum electrode with a sputtered nickel coating. In one embodiment, the hemoglobin is immobilized to the primary electrode. In one embodiment, the reference electrode is an Ag/AgCl electrode. In one embodiment, the reaction cell further comprises a counter-electrode. For example, the counter-electrode may be a platinum wire.

In one embodiment, the test sample is whole blood. In one embodiment, wherein the test sample is whole blood in an EDTA vial. In one embodiment, the reaction cell further comprises a phosphate buffered saline solution. In one embodiment, introducing the test sample into the reaction cell is by adding whole blood to the phosphate buffered saline solution.

In one embodiment, the current, voltage or resistance that is generated between the primary electrode and the reference electrode is due to the catalytic decomposition of peroxide. In one embodiment, a measured current, voltage or resistance in the test sample that is less than the reference sample indicates the presence of malaria in the subject. In one embodiment, the reduced current, voltage or resistance in the test sample is due a reduced amount of tetrameric hemoglobin compared to dimeric hemoglobin in the sample.

In one embodiment, following step (a), the primary electrode is washed. For example, the primary electrode may be washed with phosphate buffer. In one embodiment, hydrogen peroxide is added to the reaction cell at a final concentration from about 10 to about 200 mM, from about 50 to about 100 mM. In illustrative embodiment, hydrogen peroxide is added to the reaction cell at a final concentration of about 85 mM.

In one embodiment, measuring the current generated between the primary electrode and the reference electrode is by cyclic voltammetry. For example, the potential may be repetitively cycled from about −0.5 to about 0.5 V at a scan rate of 100 mV per second. In an illustrative embodiment, the potential is cycled three times.

In one embodiment, the reference level is a measured current, voltage, and/or resistance of a control sample. In one embodiment, a statistically significant difference between the test sample and the control sample indicates the presence of malaria in the subject. In one embodiment, the control sample is a whole blood sample from a known healthy subject or a population of healthy subjects.

In one aspect, the present technology provides a method for diagnosing malaria in a test sample of hemoglobin from a subject, the method comprising: (a) introducing the test sample into a first and a second reaction cell, each reaction cell comprising a primary electrode and a reference electrode; (b) adding hydrogen peroxide to the reaction cells; (c) measuring a first current generated between the primary electrode and the reference electrode in each reaction cell; (d) adding inositol hexaphosphate to the first reaction cell and 2,3-diphosphoglycerate to the second reaction cell; and (e) measuring a second current generated between the primary electrode and the reference electrode in each reaction cell, wherein the absence of a change between the first current and the second current in each reaction cell indicates a diagnosis of malaria in the subject. In one embodiment, (i) an increase between the measured first current and the second current in the first reaction cell; (ii) a decrease between the measured first current and the second current in the second reaction cell; or (iii) both (i) and (ii) indicates that the subject does not have malaria.

In one embodiment, the inositol hexaphosphate is added to the reaction cell at a final concentration from about 50 to about 250 µM. In an illustrative embodiment, the inositol hexaphosphate is added to the reaction cell at a final concentration of about 150 µM. In one embodiment, the 2,3-diphosphoglycerate is added to the reaction cell at a final concentration from about 1 to about 3 mM. In an illustrative embodiment, the 2,3-diphosphoglycerate is added to the reaction cell at a final concentration of about 2 mM.

In another aspect, the present technology provides a kit for diagnosing malaria in a subject, the kit comprising: (a) a reaction cell comprises a primary electrode and a reference electrode; (b) hydrogen peroxide; and (c) one or more allosteric modulator chemicals selected from the group consisting of: inositol hexaphosphate and 2,3-diphosphoglycerate. In an illustrative embodiment, the primary electrode is a platinum electrode with a sputtered nickel coating. In one embodiment, the reference electrode is an Ag/AgCl electrode. In one embodiment, the reaction cell further comprises a counter-electrode. In one embodiment, the counter-electrode is a platinum wire.

In one embodiment, the kit further comprises a detector configured to measure current or voltage generated between the primary electrode and the reference electrode in response to the redox reaction. In one embodiment, the kit comprises a signal-displaying device to show the current or voltage generated between the primary electrode and the reference electrode.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
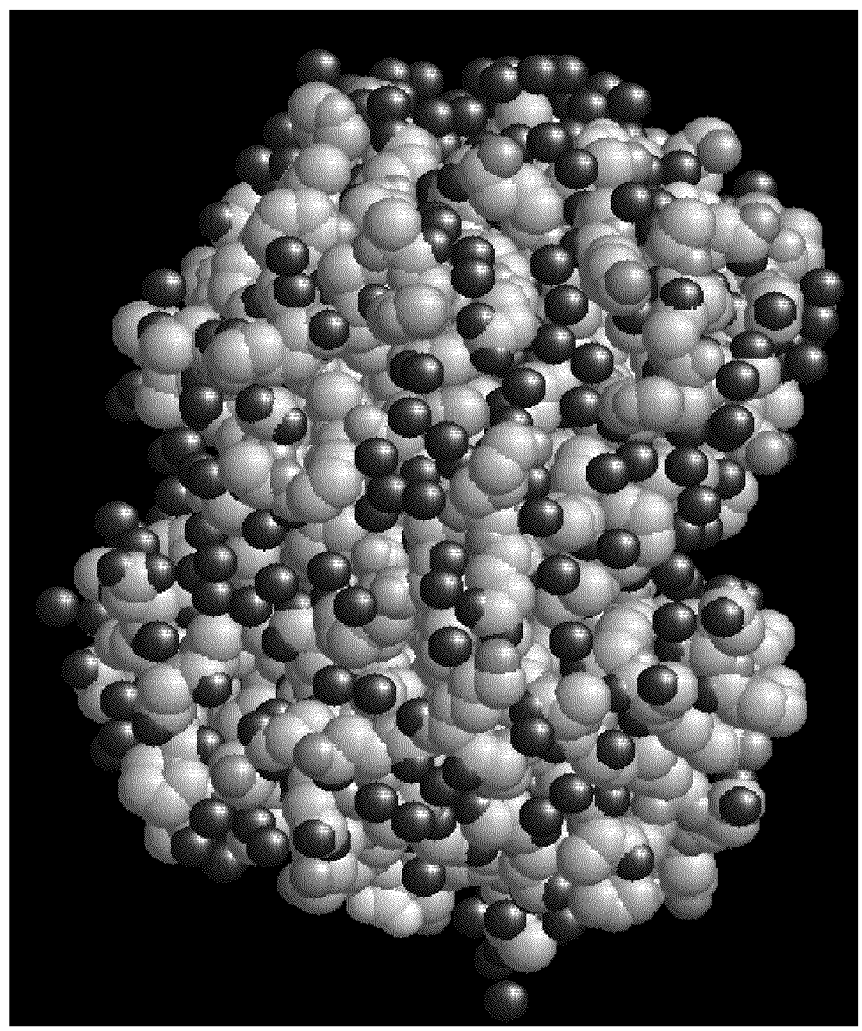
FIG. 1 is an image illustrating histidine residues on the alpha beta dimeric hemoglobin surface through Raswin PDB viewer in a space filled model. The surface exposed histidines are clearly observed through the model.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented here.

The present technology is described herein using several definitions, as set forth throughout the specification. As used herein, unless otherwise stated, the singular forms "a," "an," and "the" include plural reference. Thus, for example, a reference to "a cell" includes a plurality of cells, and a reference to "a molecule" is a reference to one or more molecules.

Disclosed herein are methods for detecting the presence or absence of *Plasmodium* infection in subjects based, at least in part, on results generated by using the testing methods described herein on samples from the subject. Further disclosed herein are methods for monitoring the status of subjects diagnosed with malaria based at least partially on results of tests on a sample. The test samples disclosed herein are represented by, but not limited in anyway to, sputum, blood (or a fraction of blood such as plasma, serum, or particular cell fractions), lymph, mucus, tears, saliva, urine, semen, ascites fluid, whole blood, and biopsy samples of body tissue. This disclosure is drawn, inter alia, to methods of diagnosing, monitoring, and treating malaria. Also provided herein are apparatuses and kits for detecting aberrant hemoglobin, biosensor systems including such apparatuses, and methods of using the biosensor systems.

Hemoglobin (Hb) is a heme protein which contains two α and two β subunits—each of which has one electroactive iron heme as a prosthetic group. Hemoglobin comprises 95% of RBC cytosolic protein and it serves as the major source of nutrients for immature intra-erythrocytic trophozoites, providing amino acids needed for Plasmodium protein synthesis. Proteins that contain a heme group, such as hemoglobin, have the ability to reduce $H_2O_2$ to $O_2$ electrocatalytically. Accordingly, this activity can be measured electrochemically.

*Plasmodium* sporozoites are transmitted by female *Anopheles* mosquitoes and are injected into the blood of a human host. After the initial proliferation in the liver, merozoites are formed which are released back into the blood stream where they invade red blood cells (RBCs). The matured parasite then enters the trophozoite stage where it catabolizes most of the RBC cytoplasm and undergoes several divisions to produce several additional merozoites that eventually burst from the host RBC and invade new erythrocytes. Upon lysis of the RBCs, hemoglobin is released in the blood stream. This hemoglobin is dimerized before it is degraded.

While not wishing to be limited by any theory, the electrocatalytic activity of the intact hemoglobin tetramer and the hemoglobin dimer formed after partial degradation by Plasmodium will be different due to the presence of multiple active heme groups. Allosteric modulators, such as 2,3-diphosphoglycerate and inositol hexaphosphate, normally affect the stability of the hemoglobin tetramer and will cause a change in the electrocatalytic activity. However, these compounds will not change the electrocatalytic activity of dimeric hemoglobin. Based on this principle, the dimeric hemoglobin from *Plasmodium*-infected subjects, i.e., patients with malaria, can be distinguished from normal hemoglobin.

Biosensors for Malaria Diagnosis

In one aspect, the present disclosure provides a biosensor to detect aberrant hemoglobin in a sample, such as dimeric hemoglobin formed as a result of a *Plasmodium* infection. In one embodiment, the biosensor comprises an electrochemical cell containing a working electrode capable of binding to hemoglobin. An electrode the is capable of binding hemoglobin typically includes a capture reagent that can bind to hemoglobin. In one embodiment, the capture reagent is a nickel coating that interacts with one or more histidine residues on the surface of hemoglobin.

As used herein, the term "electrochemical cell" refers to a device comprising a working electrode and a reference electrode which are connected to one another electrically. When in use, electrochemical reactions cause electrons to flow to and from the electrodes, thus generating a current. An electrochemical cell can be set up either to harness the electrical current produced, for example in the form of a battery, or to detect electrochemical reactions which are induced by an applied current or voltage.

The terms "working electrode" or "primary electrode" are used interchangeably to mean an electrode where the reaction of interest takes place. The current is proportional to the concentration of an analyte, e.g., hemoglobin, at the working electrode. The term "reference electrode" refers to an electrode that measures the potential at the interface of the working electrode and the sample as accurately as possible. The term "counter electrode" refers to an electrode that ensures that the correct potential difference between the reference electrode and the working electrode is being applied. The potential difference between the working electrode and the reference electrode is assumed to be the same as the desired potential at the working electrode. If the potential measured at the working electrode is not the potential desired at the working electrode, the potential that is applied between the counter electrode and the working electrode is altered accordingly, i.e., the potential is either increased or decreased. The reaction at the counter electrode is also equal and opposite to the charge transfer reaction occurring at the working electrode, i.e., if an oxidation reaction is occurring at the working electrode then a reduction reaction will take place at the counter electrode, thereby allowing the sample to remain electrically neutral. No current passes through an ideal reference electrode, and such an electrode maintains a steady potential.

There are numerous ways to prepare the electrochemical cell. The electrodes may be formed from, or coated with, a variety of materials, including, but not limited to, a conductive material such as a metal. Non-limiting examples of metals include gold, platinum, palladium, silver, copper, iridium, or cobalt. Other possible materials for the electrodes include carbon or indium tin oxide or metal compositions. In one embodiment, an insulating support is coated with a conducting material, such as carbon or conductive metal, by means of screen-printing or other deposition technique, such as sputtering, to form a first conducting layer.

In some embodiments, a variety of particles may be coupled to the primary electrode, the reference electrode, or both. By way of example only, the particles may be metallic nanoparticles. By "nanoparticle" it is meant a particle having any maximum dimension from about 0.5 nm to about 100 nm. This includes nanoparticles having any maximum dimension from about 0.5 nm to about 2 nm, from about 1 nm to about 50 nm, or from about 1 nm to about 10 nm. However, other ranges are possible. The shape of the nanoparticles may vary. Nanoparticles may be spherical in shape, but other shaped nanoparticles are possible, including, but not limited to nanorods, nanowires, and nanotubes. The metallic nanoparticles may be formed from a variety of metals including, but not limited to silver, gold, iron, platinum, and combinations thereof. Metallic nanoparticles are commercially available or may be made using known methods. In one embodiment, the nanoparticles are spherical nickel nanoparticles having a mean diameter from 10-50 nm.

In an illustrative embodiment, the working electrode is a platinum electrode with a sputtered nickel coating. For example, the sputtered nickel coating may be a 20 nm thick nickel coating. In one embodiment, hemoglobin is immobilized to a nickel-coated electrode via the histidine residues on the surface of hemoglobin. This binding allows the protein to attach to the electrode through a single α/β dimeric interface.

The particles, including metallic nanoparticles, may be coupled to the primary electrode and/or the reference electrode by one or more linker molecules. A variety of linker molecules are possible, provided that the linker molecule is capable of conducting electrons and is capable of binding to the electrode at one end and the particle at the other end. By way of example only, linker molecules comprising thiol groups are capable of binding to metals such as gold, silver, nickel, and platinum. Linkers include, but are not limited to, regioregular poly-3-hexylthiophene (regP3HT) and dithiobisscuccinimidyl propionate (DTSP). See Pandey, P., "Polythiophene gold nanoparticles composite film for application to glucose sensor," Journal of Applied Polymer Science, 110: 988-994, 2008. Linker molecules are commercially available or may be made using known methods. Methods and conditions for reacting the linker molecules to the particles and electrodes are also known.

Any of the reaction cells disclosed above can be incorporated into a biosensor system. The biosensor systems include a reaction cell and a detector. The detector is configured to measure current or voltage generated between the primary electrode and the reference electrode in response to a redox reaction of hemoglobin on the working electrode. The reaction cell may include a housing adapted to encompass the various components of the reaction cell and to contain the sample including the hemoglobin. The shape, size, and materials used for the reaction cell are not critical provided they are compatible with the components of the apparatus and the hemoglobin sample. The working electrode and the reference electrode may be electrically coupled through a variety of means, including, but not limited to, a wire.

The disclosed apparatuses can be configured to measure current or voltage between the working electrode and the reference electrode in response to a electrocatalytic redox reaction between hemoglobin coupled to the working electrode and hydrogen peroxide. By way of example only, the biosensor can include a detector electrically coupled to the working and reference electrodes such as a voltmeter for measuring voltage or an ammeter for measuring current. The biosensor systems may further include a signal-displaying device to show the current or voltage generated between the primary electrode and the reference electrode. The signal-displaying device may also be programmed to show the results of a diagnostic assay, e.g., "malaria infection present" or "malaria infection no present." A variety of signal-displaying devices may be used including, but not limited to LCD displays. The biosensor can also include other standard components used in electrochemical cells.

The biosensor systems may also include an inlet for introducing the sample to the reaction cell. Any method of introducing liquid samples to the reaction cell can be used. The dimensions of the passage suitable for uptake of sample by capillary attraction can be specified. Other methods, such as, for example, gravitational forces, chemically-aided wicking, or suction by means of vacuum, can be used. In certain applications, the passage can be filled with a porous material that will allow uptake of the sample by wicking.

In some embodiments, a signal-displaying device is also capable of supplying an electrical potential difference between the working electrode and the reference electrode of a magnitude sufficient to cause electrochemical oxidation. The device should be capable of supplying an electrical potential difference between the reference electrode and the counter electrode of a magnitude sufficient to facilitate the flow of electrons from the working electrode to the counter electrode. In addition, the device should be capable of measuring the current produced by the redox reaction at the working electrode.

There are a variety of voltage-based electrochemical fluid analysis techniques, e.g., voltammetric techniques such as cyclic voltammetry (CV), square wave voltammetry (SWV), linear scan voltammetry (LSV), differential pulse voltammetry (DPV), and normal pulse voltammetry (NPV), and time based techniques such as modified chronoamperometry (MCA). Generally, in each of these techniques, a fixed or slowly varying DC voltage is applied between either two or three electrodes of an electrochemical cell and measurements of the resulting current are plotted as a function of voltage and/or time.

In one embodiment, a constant voltage is applied at the working electrode with respect to the reference electrode, and the current between the working and counter electrodes is measured. The response of the electrochemical cell has two components, catalytic and Faradaic (solution resistance component). If the resistance of the solution is minimized, the response of the electrochemical cell at any given time will have a substantially higher catalytic component, as compared with the solution resistance component. Therefore, one should be able to obtain good correlation with the amount of hemoglobin from the response of the electrochemical cell even at assay times as short as one second.

Figure 6:
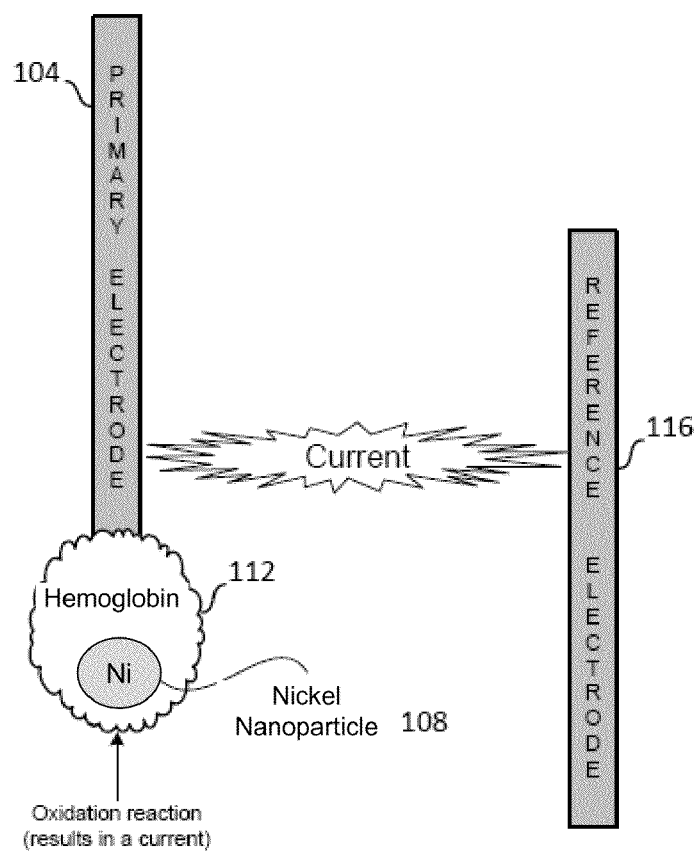
FIG. 6 depicts an illustrative embodiment of an apparatus for detecting hemoglobin.

FIG. 6 depicts an illustrative embodiment of a reaction cell for detecting hemoglobin. The term "detecting" is meant to encompass one or more of determining the presence of hemoglobin (including dimeric and/or tetrameric hemoglobin), determining the concentration, and/or determining the amount of hemoglobin (including dimeric and/or tetrameric hemoglobin). The apparatus 100 of FIG. 6 includes a primary electrode and hemoglobin immobilized on the electrode via a nickel nanoparticle 108. The apparatus 100 further includes a reference electrode 116. The apparatus 100 is configured to measure the current generated between the primary electrode 104 and the reference electrode 116 in response to a redox reaction of the hemoglobin 112 in the presence of $H_2O_2$. In the presence of hemoglobin 112, the reduction of $H_2O_2$ is catalyzed, and a current is generated. The nickel nanoparticle provides an electrical pathway between the redox center of the hemoglobin and the electrode. The current can be quantitatively measured against the reference electrode 116. The generation of a current signal provides an indication of the presence of the hemoglobin and the magnitude of the current signal provides an indication of the concentration of the hemoglobin. In some embodiments, the reaction cells are reusable. The reaction cells should be kept in proper buffering conditions and temperature, e.g., immersed in phosphate-buffered saline at 4° C.

Methods

The disclosed reaction cells and biosensor systems may be used in a variety of applications. One application involves a method for detecting an aberrant hemoglobin in an assayed sample. By "aberrant hemoglobin" is meant any mutant or variant hemoglobin, such as those found in malaria, sickle cell disease, and thalassemia, among others. In one embodiment, the aberrant hemoglobin is dimeric hemoglobin released from red blood cells after a Plasmodium infection. The terms "determining," "assessing," "measuring," "detecting," and "assaying" are used interchangeably to refer to any form of measurement, and include determining if a characteristic, trait, or feature is present or not. Assessing may be relative or absolute. "Assessing the presence of" may include determining the amount of something present, as well as determining whether it is present or absent.

One application for the disclosed biosensor systems includes methods for diagnosing malaria in a subject. As used herein, the term "diagnosis" means detecting a disease or disorder or determining the stage or degree of a disease or disorder. The term "diagnosis" also encompasses determining the therapeutic effect of a drug therapy, or predicting the pattern of response to a drug therapy. The diagnostic methods may be used independently, or in combination with other diagnostic and/or staging methods known in the medical art for a particular disease or disorder, e.g., malaria.

The methods include introducing a sample to be assayed into the reaction cell of any of the disclosed biosensor systems and measuring the current or voltage generated between the primary electrode and the reference electrode of the biosensor system. The generation of a current or voltage provides an indication that hemoglobin is present in the assayed sample. In addition, the magnitude of the current or voltage provides an indication of the concentration and/or tertiary form of the hemoglobin in the assayed sample. For instance, the magnitude of the current or voltage may be an indication of the relative amount of dimeric versus tetrameric hemoglobin in the sample. The relative amount of dimeric versus tetrameric hemoglobin can be determined by comparing the measured current or voltage generated from the assayed sample to a reference level. As used herein, the term "reference level" refers to an amount of current, voltage, and/or resistance which may be of interest for comparative purposes. In one embodiment, a reference level may be the level of current, voltage, and/or resistance expressed as an average of the level of the current, voltage, and/or resistance from samples taken from a control, such as a sample from one or more healthy subjects, or a sample having known concentrations of dimeric or tetrameric hemoglobin or mixtures thereof. In another embodiment, the reference level may be the level of current, voltage, and/or resistance in the same subject at an earlier time, i.e., before the present assay. In even another embodiment, the reference level may be the level of current, voltage, and/or resistance in the subject prior to receiving a treatment regime.

In some embodiments, a comparison between the measured current, voltage, and/or resistance of a test sample and the reference level reveals a difference between the values. As used herein, the phrase "difference of the level" refers to differences in the measured current, voltage, and/or resistance of a test sample using the reaction cells described herein as compared to a reference level. The measured current, voltage, and/or resistance may be observed at an elevated amount or at a decreased amount in samples from malaria patients compared to a reference level. In one embodiment, a "difference of a level" may be a difference between the current, voltage, and/or resistance measured for a test sample as compared to a reference level of at least about 1%, at least about 2%, at least about 3%, at least about 5%, at least about 10%, at least about 15%, at least about 20%, at least about 25%, at least about 30%, at least about 35%, at least about 40%, at least about 50%, at least about 60%, at least about 75%, at least about 80% or more. In one embodiment, a "difference of a level" may be a statistically significant difference between the current, voltage, and/or resistance measured for a test sample as compared to a reference level. For example, a difference may be statistically significant if the current, voltage, and/or resistance measured for a test sample falls outside of about 1.0 standard deviations, about 1.5 standard deviations, about 2.0 standard deviations, or about 2.5 stand deviations of the mean of any control or reference group.

In one embodiment, the method can further include comparing the measured current or voltage generated from the assayed sample to a standard curve to determine the absolute amount of hemoglobin in the sample. The standard curve may be created using known amounts of dimeric hemoglobin, tetrameric hemoglobin or mixtures thereof. For example, a standard curve may be generated by measuring the electrical current or voltage generated from samples of known concentrations of tetrameric hemoglobin. The voltage or current generated in test samples may then be compared to the standard curve.

A variety of samples may be analyzed by the disclosed methods, including the blood of a subject. As used herein, the term "sample" may include, but is not limited to, bodily tissue or a bodily fluid such as blood (or a fraction of blood such as plasma or serum), lymph, mucus, tears, saliva, sputum, urine, semen, stool, CSF, ascities fluid, or whole blood, and including biopsy samples of body tissue sample may be obtained from any subject, e.g., a subject/patient having or suspected to have malaria, i.e. a *Plasmodium* infection. In one embodiment, a sample is a bodily fluid that contains hemoglobin.

Methods of plasma and serum preparation are well known in the art. Either "fresh" blood plasma or serum, or frozen (stored) and subsequently thawed plasma or serum may be used. Frozen (stored) plasma or serum should optimally be maintained at storage conditions of −20 to −70° C. until thawed and used. "Fresh" plasma or serum should be refrigerated or maintained on ice until used. Exemplary methods are described below.

Blood can be drawn by standard methods into a collection tube, typically siliconized glass, either without anticoagulant for preparation of serum, or with EDTA, sodium citrate, heparin, or similar anticoagulants for preparation of plasma. If preparing plasma or serum for storage, although not an absolute requirement, is that plasma or serum is first fractionated from whole blood prior to being frozen. "Fresh" plasma or serum may be fractionated from whole blood by centrifugation, using gentle centrifugation at 300-800 times gravity for five to ten minutes, or fractionated by other standard methods. Heparin or EDTA may be added to prevent the coagulation of blood specimens.

In one embodiment, the liquid sample can be a sample of whole blood. In other embodiments, the liquid sample can be whole blood that has been filtered or treated to remove red blood cells or other hemocytes. A number of diagnostic tests are routinely performed on humans to evaluate the amount or existence of substances present in blood or other body fluids. These diagnostic tests typically rely on physiological fluid samples removed from a subject, either using a syringe or by pricking the skin. In another embodiment, the sample may be a sample of lysed blood. For example, it may be useful to pre-treat a blood sample by collecting the relatively large blood cells on a filtration membrane. After rinsing the collected cells with saline to remove adhering proteins, the cell membranes may be ruptured by exposing them to deionized water or a detergent. In this manner, the dissolved hemoglobin will pass through the filtration membrane. The cell membranes will remain on the filter paper.

By "subject," it is meant any animal, including mammals, e.g., a human, a primate, a dog, a cat, a horse, a cow, a pig, or a rodent, e.g., a rat or mouse. The subjects may be normal, healthy subjects or subjects having, or at risk for developing, a particular biological disease or condition. By way of example only, the subject may be a subject having, or at risk for developing, malaria, i.e., a *Plasmodium* infection. The term "patient" refers to a "subject" who is, or is suspected to be, afflicted with malaria.

Another application involves a method for diagnosing malaria in a subject. The methods can include associating the presence of aberrant hemoglobin and/or particular concentrations of the aberrant hemoglobin with a biological disease or condition. As discussed above, dimeric hemoglobin may be associated with malaria. Thus, detection of such hemoglobin can indicate the presence of malarial infection in the subject because the hemoglobin dimer is formed after partial degradation by *Plasmodium*.

In one embodiment, a test sample from a subject having or suspected of having malaria is tested for aberrant hemoglobin using the biosensor described above. This assay is based on the observation that particular forms of hemoglobin are associated with *Plasmodium* infection due to the action of the pathogen on red blood cells. The method includes introducing a test sample, e.g., blood or a fraction thereof, from a test subject into the reaction cell of any of the disclosed biosensor systems; measuring the current or voltage generated between the primary electrode and the reference electrode of the biosensor system; and comparing the measured current or voltage generated from the test sample of the subject to the measured current or voltage generated from a subject free of malaria (See FIG. 7). The presence of certain aberrant hemoglobin and/or the concentration of certain aberrant hemoglobin in the blood of the test subject as compared to that of the subject free malaria can indicate the presence of malaria. In particular, a statistically significant difference in the measured currents or voltages of the blood of the test subject and the blood of the subject free of malaria can indicate the presence of malaria.

Figure 8:
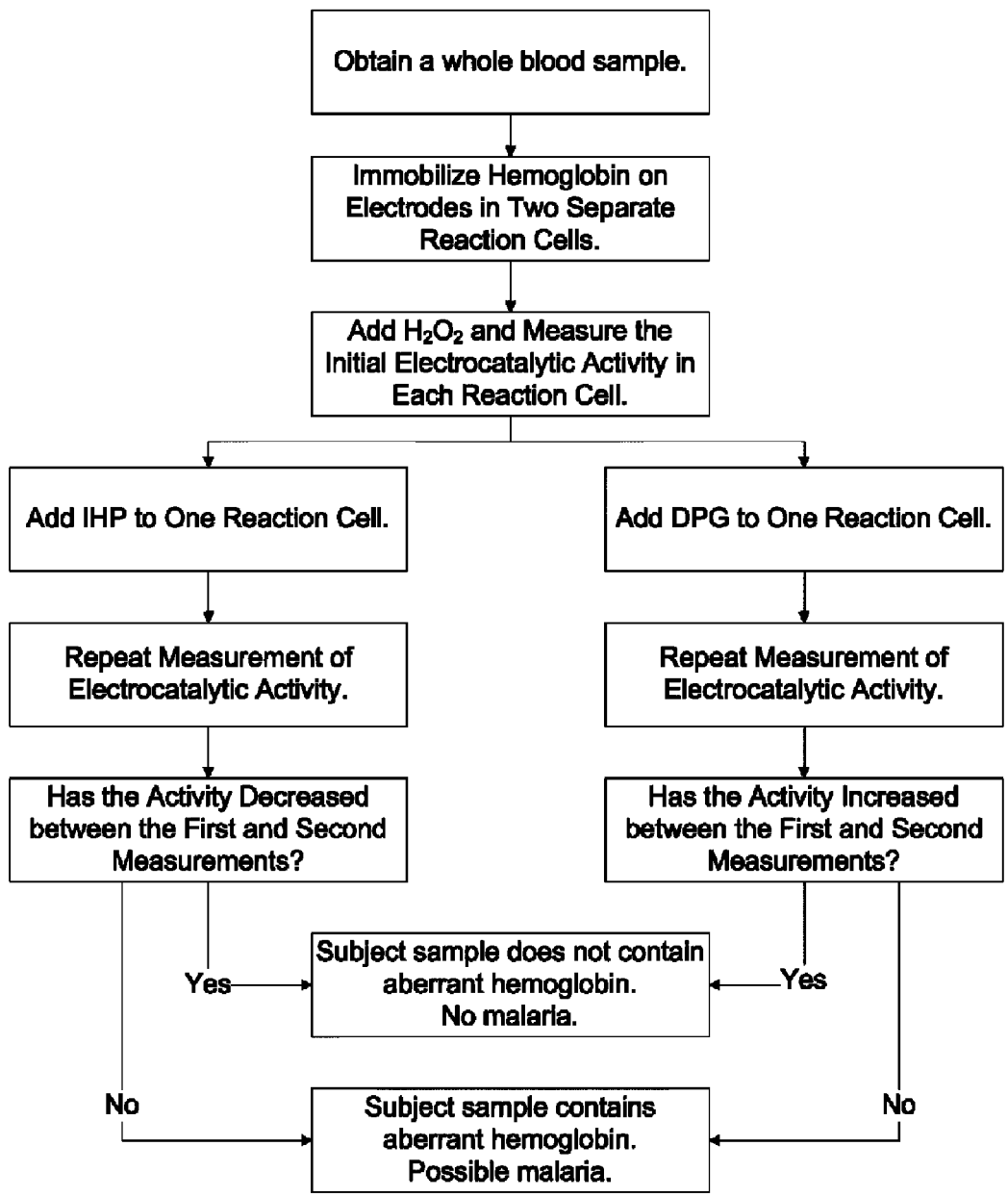
FIG. 8 is a flow chart of a second illustrative embodiment of a sample collection and assay procedure.
Figure 7:
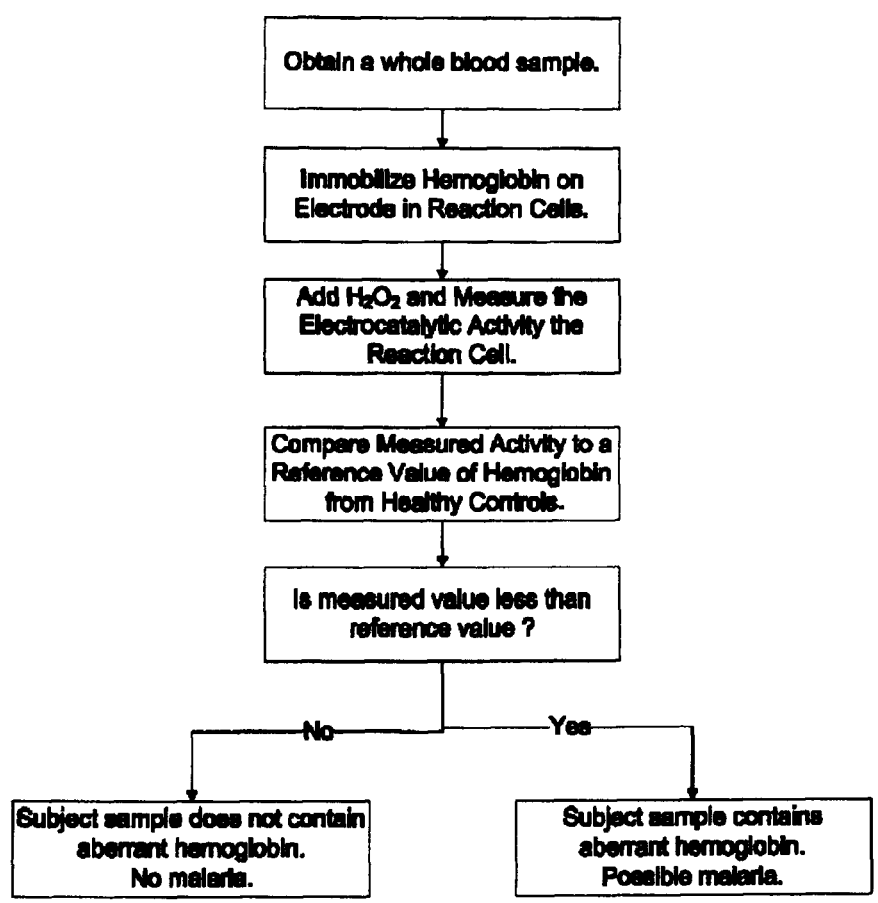
Figure 7:
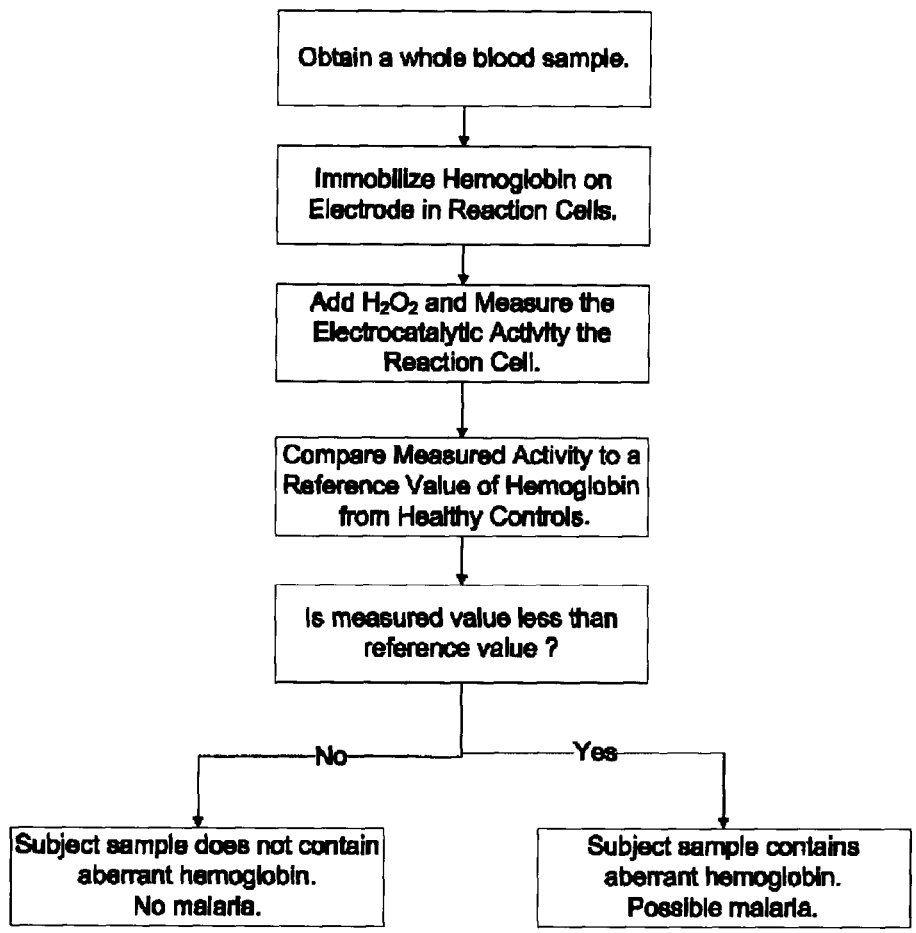

Another application involves a method for diagnosing malaria in a subject by measuring the effect of certain allosteric modulators on a sample containing hemoglobin obtained from the subject (See FIG. 8). Inositol hexaphosphate (IHP) shifts the equilibrium of tetramer-dimer of reduced hemoglobin (HbA0) towards the dimer form. Consequently, if all or some of the hemoglobin in a malaria patient is already in the dimeric form, IHP will have less of an effect on the measured current or voltage compared to normal tetrameric hemoglobin.

2,3 diphosphoglycerate (2,3-DPG) is known to stabilize the tetrameric structure of hemoglobin and prevent dimerization. The stabilization of the immobilized HbA0 by 2,3 DPG will result in higher electrocatalytic activity in normal samples hemoglobin due to the presence of more tetrameric protein molecules. Dimeric hemoglobin from malaria patients will not be stabilized. In summary, IHP decreases electrocatalytic activity in tetrameric hemoglobin and 2,3 DPG increases the same by stabilizing the tetrameric structure from auto dimerization (Table 1). These characteristics in the presence of allosteric modulators are not observed in samples of hemoglobin obtained from malaria patients.

TABLE 1

Difference from normal healthy individual to detect the infected samples.

| Chemical Name | Electrocatalytic Activity in Healthy HbA0 | Electrocatalytic Activity in Malaria-Infected HbA0 |
| --- | --- | --- |
| IHP | Decrease | No change |
| 2,3-DPG | Increase | No change |

EXAMPLES

The present disclosure is further illustrated by the following examples, which should not be construed as limiting in any way.

Example 1

Cyclic Voltammetry Study to Elucidate Urea Induced Hemoglobin Unfolding and Subunit Dissociation This Example describes a new electrochemical approach to investigate the complex unfolding of the multimeric protein hemoglobin. The experiments demonstrate the possibility of this technique to distinguish between the subunit dissociation and extended structure formation due to unfolding of the protein, which is very challenging by conventional methods. This approach provides a simple method to study the complex phenomena involved in the unfolding of redox active proteins.

Materials and Methods

Hemoglobin Preparation. Crystal ferrous human hemoglobin (HbA0) was obtained from Sigma chemicals (H-267). The stock solution was prepared by dissolving 5 mg HbA0 in one milliliter of 0.05 M phosphate buffered saline (pH 7.2) (Sigma chemicals).

Fabrication Of Nickel Coated Electrode Chips For Hemoglobin Immobilization. Standard p-doped 4-inch silicon wafers (1-10 Ohm cm) were oxidized under wet conditions (1000° C.) to grow 1000 nm of insulating silicon dioxide. Subsequently, a 15 nm titanium adhesion layer and 200 nm platinum were deposited as an electrode material using electron beam evaporation. On top of the platinum layer a 15 nm nickel coating was sputtered to facilitate histidine binding on the electrode surface. The wafers were cut into individual chips of 11×11 cm$^2$ size, which fitted into our homebuilt electrochemical cell.

Electrochemical Measurements. For the electrochemical experiments we used a computer controlled Autolab (PG-STAT) modular electrochemical system (Eco Chemie Ultecht, The Netherlands) that was operated with GPES software (Eco Chemie). All experiments were performed in a conventional three-electrode system cell with an Ag/AgCl reference electrode (BAST), a Pt wire as counter electrode, and a nickel coated chip as working electrode at ambient room temperature (21° C.).

Immobilization Of Hemoglobin On The Chip Surface And Cyclovoltammetric Measurements. Cyclic voltammetry was used for the immobilization of hemoglobin onto nickel coated electrodes following a similar approach as Salimi et al. To immobilize hemoglobin on the electrode surface, the electrodes were immersed in fresh 0.05 M phosphate buffer solution (pH 7.2) containing 5 mg ml-1 hemoglobin and the potential was repetitively cycled (30 scans) from 1 to −0.5 V vs. Ag/AgCl at a scan rate of 100 mV s$^{-1}$. After immobilization, the chips were washed thoroughly with phosphate buffer and subsequently subjected to cyclovoltammetric measurements in the presence of 0-8 M urea.

Unfolding Study Of Hemoglobin Through Peroxidase Activity Measurements By Cyclic Voltammetry. After hemoglobin immobilization the chips were incubated in presence of 0-8 M urea for 30 min. Hydrogen peroxide (85 mM) was added to monitor the peroxidase activity change for the unfolded protein. All the experiments were performed with the setup described for electrochemical measurements. The potential was repetitively cycled (3 scans) from −0.5 to 0.5 V vs. Ag/AgCl at a scan rate of 100 mV s$^{-1}$. In a control experiment the same electrochemical measurements were performed on a reference chip without immobilized hemoglobin.

Shifting Of The Tetramer Dimer Equilibrium And Electrochemical Measurements. In a control experiment, after the immobilization of hemoglobin on the chip, the tetramer dimer equilibrium was shifted towards dimer by inositol hexaphosphate at a final concentration of 150 µM and electrochemical measurements were performed. The potential was repetitively cycled (3 scans) from −0.5 to 0.5 V vs. Ag/AgCl at a scan rate of 100 mV s$^{-1}$ as described before. The peroxidase activity of hemoglobin was also measured under this condition by adding 85 mM hydrogen peroxide. In another control experiment, the same electrochemical and peroxidase activity measurements were performed on immobilized hemoglobin in presence of the tetramer stabilizer 2,3-DPG at a final concentration of 2 mM.

Results

Figure 2:
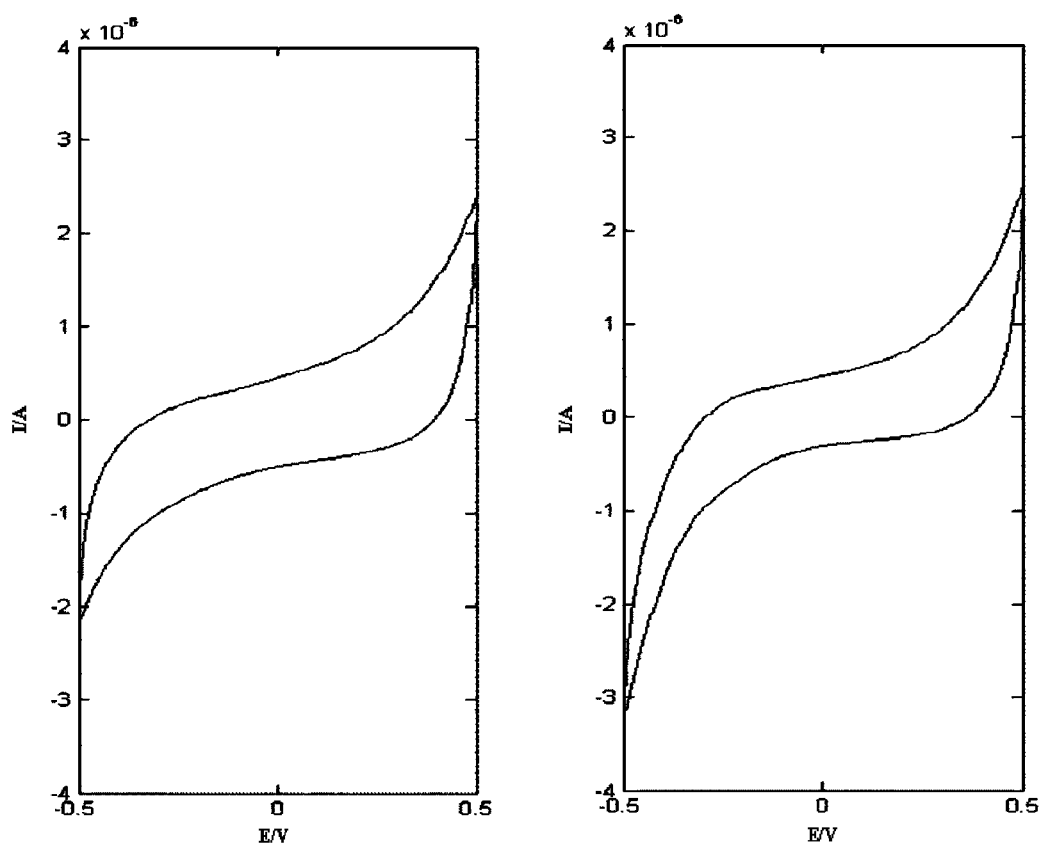
FIG. 2 is an graph of an illustrative cyclic voltammogram of a nickel coated control electrode and an electrode with immobilized hemoglobin. The left panel shows the plot of the control electrode and the right panel for the immobilized hemoglobin.

In this study, the goal was to compare the unfolding profile of the multimeric protein hemoglobin in presence of urea in solution and after immobilization on an electrode surface. The method used for protein binding on electrodes was based on the strong affinity of the amino acid histidine towards a nickel surface. The structure of the oxy hemoglobin dimer (alpha-beta) from the Protein Data Base (PDB Id: 2DN1) visualized through PDB viewer is shown in FIG. 1. The histidine residues that are exposed to the outer surface are marked on the structure. Thus, the approach for immobilizing hemoglobin A0 onto the electrode relied on the binding of these outer histidine molecules on a nickel coated surface. As a control experiment FIG. 2 shows two cyclic voltammograms of nickel coated electrodes in phosphate buffered saline with (a) and without (b) immobilized HbA0. The potential was repetitively cycled (3 scans) from −0.5 to 0.5 V vs. Ag/AgCl at a scan rate of 100 mV s$^{-1}$ at 21° C. The curves represent the averaged current from the three cycles. As can be seen from the figure, the cyclic voltammogram of the control chip and the chip with immobilized hemoglobin did not show any significant difference in comparison to the heme peroxidase activity study explained below. This control experiment provided us the platform to carry out the activity measurements on the electrode in presence of urea.

Figure 3:
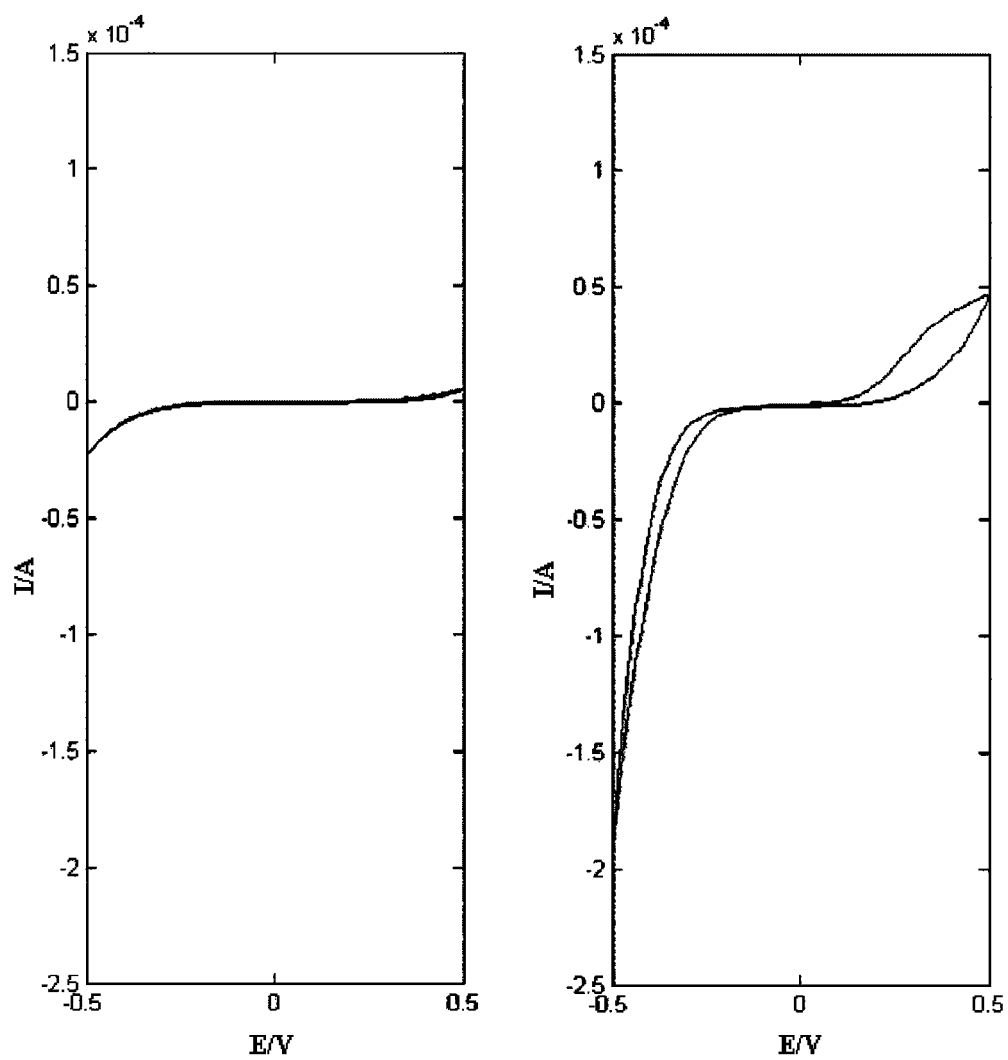
FIG. 3 is an graph of an illustrative cyclic voltammogram of the peroxidase activity in presence of hydrogen peroxide for the nickel coated control electrode and the electrode with immobilized hemoglobin. The left panel represents the activity of the control electrode and the right panel for the immobilized hemoglobin.

To electrochemically monitor the peroxidase activity of immobilized hemoglobin, cyclic voltammetry experiments were performed in the presence of $H_2O_2$. FIG. 3 (left panel) shows a control experiment with a bare nickel coated electrode while FIG. 3 (right panel) shows the response of a hemoglobin electrode. It can be seen that the hemoglobin electrode exhibits a strong reductive current below −300 mV and an oxidative current above 300 mV. This pronounced signal is caused by the peroxidase activity of hemoglobin in the presence of $H_2O_2$. It indicates the presence and functionality of hemoglobin on the electrode.

Figure 4:
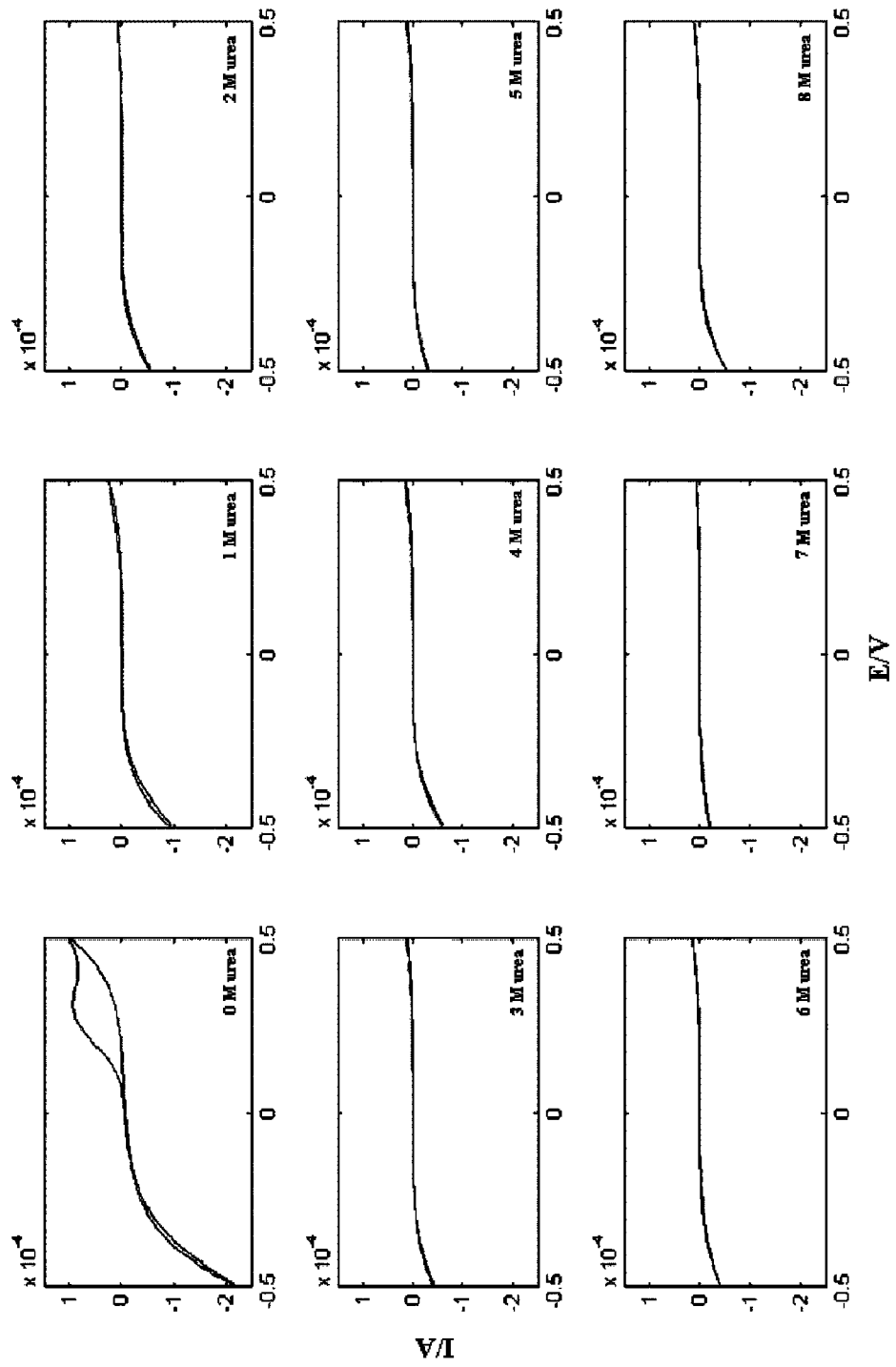
FIG. 4 is an graph of an illustrative cyclic voltammogram of the peroxidase activity in presence of hydrogen peroxide for hemoglobin immobilized on top of nickel coated electrodes in presence of 0-8 M urea. The first row represents the activity of the electrode in presence of 0-2 M urea, the second row in presence of 3-5 M urea, and the last row in presence of 6-8 M urea.

The next step was to study the urea-induced unfolding of immobilized hemoglobin electrochemically. However, to exclude possible interference of urea on the electrochemistry of the nickel electrodes, the cyclic voltammograms of chips were recorded without immobilized hemoglobin in the presence of varying urea concentration after 30 mins of incubation. The control chips showed no significant dependence of the electrochemical current on urea concentrations. FIG. 4 represents the cyclic voltammograms showing the peroxidase activity of a hemoglobin immobilized chip in the presence of 0-8 M urea after 30 mins of incubation. A decrease in electrochemical current is observed at higher urea concentrations.

Figure 5:
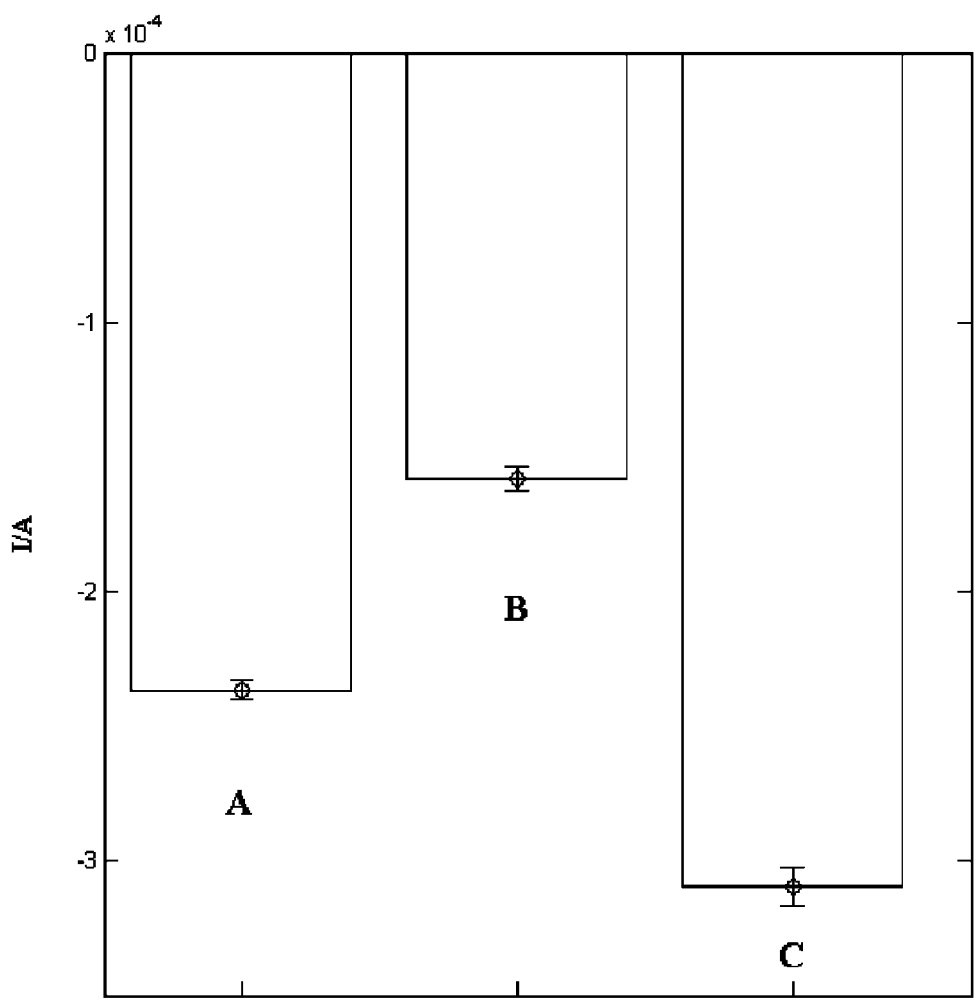
FIG. 5 is an illustrative representation of the hydrogen peroxide activity measured from the cyclovoltammetry study of immobilized hemoglobin in presence of different allosteric modulators. Panel A shows the peroxidase activity of the hemoglobin control. Panel B shows the peroxidase activity of the hemoglobin in presence of HIP. Panel C shows the peroxidase activity of the hemoglobin in presence of 2,3 DPG.

To investigate the possibility of dimerization induced loss in activity due to the detachment of the dimer from the immobilized tetrameric form, inositol hexaphosphate (IHP) was used, which increases the rate of dimerization and also observed the decrease in the peroxidase activity. In a complementary experiment, the tetrameric structure was stabilized with 2,3-DPG, and the activity was increased. The results are shown in FIG. 5. Panel A shows the peroxidase activity of the hemoglobin control. Panel B shows the peroxidase activity of the hemoglobin in presence of IHP. Panel C shows the peroxidase activity of the hemoglobin in presence of 2,3 DPG. These results show that IHP shifts the equilibrium of tetramer-dimer of HbA0 towards the dimer formation. Moreover, when the immobilized HbA0 was stabilized by 2,3 DPG, a higher peroxidase activity was observed than the normal HbA0 as shown in FIG. 5 due to the presence of more tetrameric protein molecules. As such, the electrochemical sensors described herein can be used to detect the relative amount of tetrameric/dimeric hemoglobins in a sample.

Example 2

Preparation of an Electrochemical Cell for Malaria Assays

Standard p-doped wafers having specific resistance 1-10 Ohm-cm are taken and oxidized at 1000° C. under wet conditions. 1000 nm of insulating silicon dioxide are grown on top of the wafer. Subsequently, a 10-15 nm titanium adhesion layer and 150-180 nm platinum is deposited by electron beam evaporation. The platinum will act as an electrode material. To facilitate histidine binding on the electrode surface a 20 nm nickel coating is sputtered on the top. Thus, the reaction cell includes a conventional three-electrode system cell with an Ag/AgCl reference electrode, a Pt wire as counter electrode and a nickel coated chip as working electrode.

To immobilize hemoglobin on the electrode surface, the electrodes are immersed in fresh phosphate buffer saline solution (pH 7.2) containing 4 ml of the whole blood (collected in an EDTA vial or heparinized). After immobilization, the chips are washed thoroughly with phosphate buffer. The potential is repetitively cycled (30 scans) from 1 to −0.5 V vs. Ag/AgCl at a scan rate of 100 mV s$^{-1}$.

Example 3

Measuring the Electrocatalytic Activity of Hemoglobin

Figure 7:
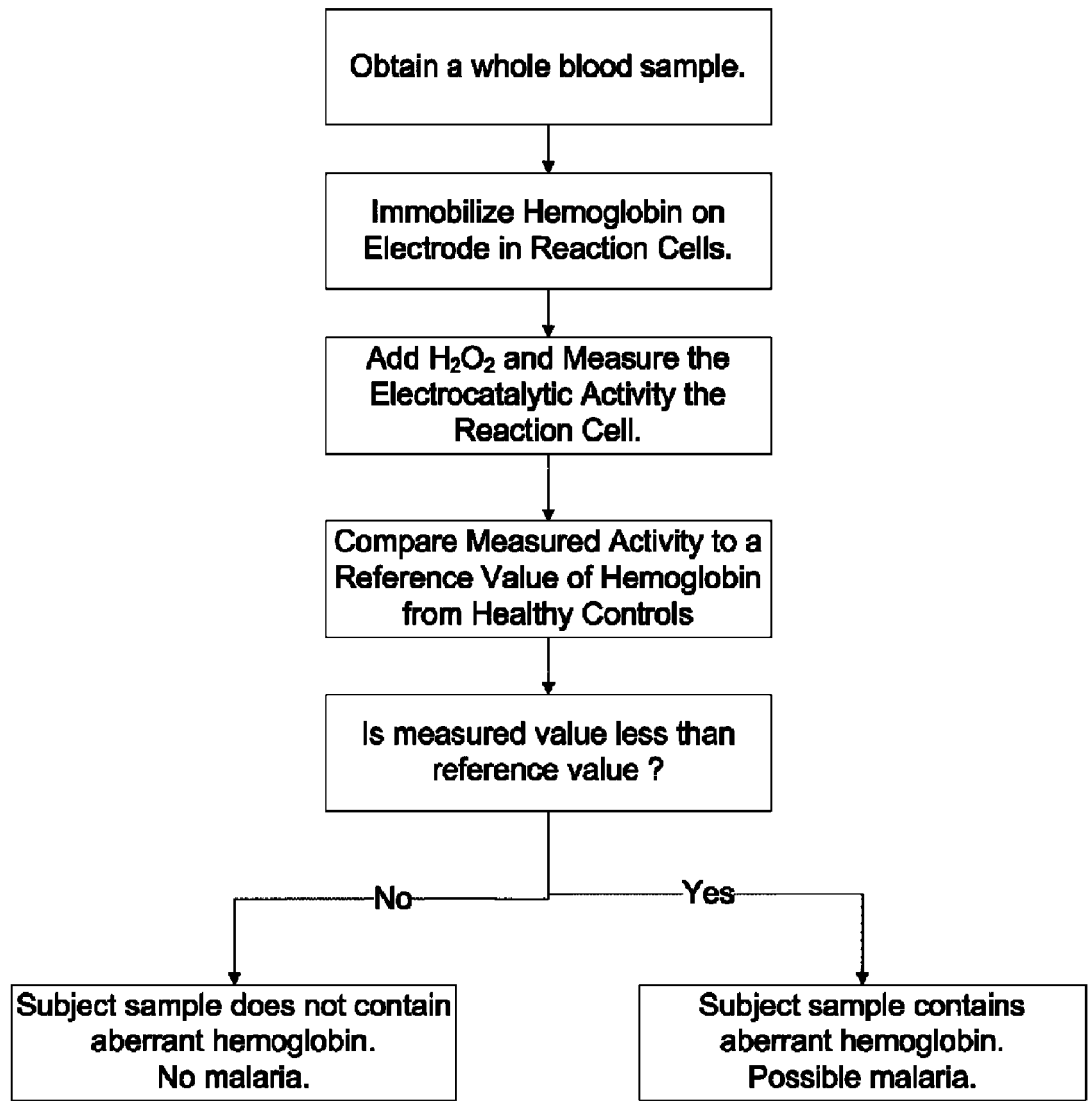
FIG. 7 is a flow chart of a first illustrative embodiment of a sample collection and assay procedure.

The assay of this example is illustrated in FIG. 7. Hemoglobin from whole blood of test and control subjects is immobilized to the surface of electrodes as described in Example 1. Hydrogen peroxide at a final concentration of 85 mM is added and the electrocatalytic activity change is monitored for the immobilized protein. The potential is repetitively cycled (3 scans) from −0.5 to 0.5 V vs. Ag/AgCl at a scan rate of 100 mV s$^{-1}$, which is sufficient for the measurements. This device is linked to a computer to record the current. The amount of current in the test sample can be compared to the control sample. Alternatively, the concentration of hemoglobin in the sample can be determined using a standard curve. It is believed that samples from subjects with malaria will produce less current at the working electrode compared to control subjects because those subjects have less tetrameric hemoglobin in their blood.

Example 4

Measuring the Electrocatalytic Activity of Hemoglobin in the Presence of Allosteric Modulators 2,3-Diphosphoglycerate and Inositol Hexaphosphate The assay of this example is illustrated in FIG. 8. Hemoglobin from whole blood of test subjects is immobilized to the surface of electrodes in two separate reaction cells as described in Example 1. Hydrogen peroxide at a final concentration of 85 mM is added in PBS to monitor the electrocatalytic activity for the immobilized protein. All the experiments are performed with the setup described above. The potential is repetitively cycled (3 scans) from −0.5 to 0.5 V vs. Ag/AgCl at a scan rate of 100 mV s$^{-1}$. This device is linked to a computer to record the current.

Next, inositol hexaphosphate (IHP) is added to one of the reaction cells at a final concentration of 150 µM. IHP is used to shift the tetramer/dimer equilibrium completely towards dimer. The effects are visualized through electrochemical measurements when the potential is repetitively cycled (3 scans) from −0.5 to 0.5 V vs. Ag/AgCl at a scan rate of 100 mV s$^{-1}$. It is believed that current measured by the oxidation at the electrode surface will decrease in hemoglobin samples from healthy subjects after the addition of IHP, but there will not be a significant change in current in hemoglobin samples from malaria patients.

2,3 diphosphoglycerate (2,3-DPG) is added to the second reaction cell at a final concentration of 2 mM. The stabilization of the immobilized HbA0 by 2,3-DPG, will result in higher electrocatalytic activity than normal due to the presence of more tetrameric protein molecules. Thus, it is believed that current measured at the electrode surface will increase in hemoglobin samples from healthy subjects after the addition of 2,3-DPG, but there will not be a significant change observed in hemoglobin samples from malaria patients because fewer tetrameric molecules are present in these samples.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 particles refers to groups having 1, 2, or 3 particles. Similarly, a group having 1-5 particles refers to groups having 1, 2, 3, 4, or 5 particles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference in their entireties and for all purposes to the same extent as if each individual publication, patent, or patent application was specifically and individually incorporated by reference in its entirety for all purposes.

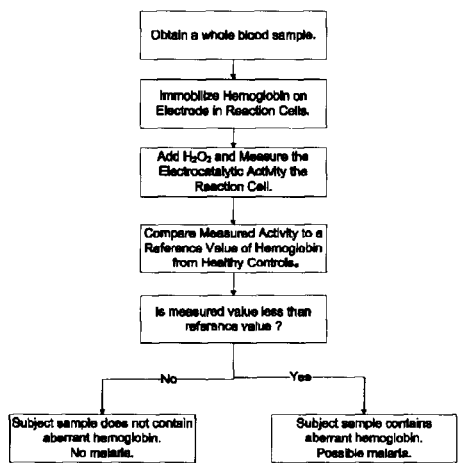

What is claimed is:

1. A method for diagnosing malaria in a subject comprising:
    introducing a test sample containing hemoglobin from the subject into a reaction cell including a primary electrode and a reference electrode;
    adding hydrogen peroxide to the reaction cell;
    measuring a current, voltage and/or resistance between the primary electrode and the reference electrode; and
    comparing the level of the measured current, voltage and/or resistance of the test sample to a reference level, wherein a difference between the reference level and the level of the measured current, voltage and/or resistance indicates the presence of malaria in the subject.

2. The method of claim 1, wherein the electrodes are each independently made of or coated by a material selected from gold, platinum, palladium, silver, carbon, copper, iridium, cobalt, nickel, or indium tin oxide.

3. The method of claim 2, wherein the primary electrode is made of or totally or partially coated with nickel.

4. The method of claim 3, wherein the hemoglobin is immobilized to the primary electrode.

5. The method of claim 2, wherein the primary electrode is a platinum electrode with a sputtered nickel coating.

6. The method of claim 2, wherein the reference electrode is an Ag/AgCl electrode.

7. The method of claim 1, wherein the reaction cell further comprises a counter-electrode.

8. The method of claim 7, wherein the counter-electrode is a platinum wire.

9. The method of claim 1, wherein the test sample is whole blood.

10. The method of claim 9, wherein introducing the test sample into the reaction cell is by adding whole blood to the phosphate buffered saline solution.

11. The method of claim 1, wherein hydrogen peroxide is added to the reaction cell at a final concentration from about 10 to about 200 mM.

12. The method of claim 1, wherein measuring the current generated between the primary electrode and the reference electrode is by cyclic voltammetry.

13. The method of claim 12, wherein the potential is repetitively cycled from about −0.5 to about 0.5 V at a scan rate of 100 mV per second.

14. The method of claim 1, wherein the reference level is a measured current, voltage, and/or resistance of a control sample.

15. The method of claim 14, wherein a statistically significant difference between the test sample and the control sample indicates the presence of malaria in the subject.

16. A method for diagnosing malaria in a test sample of hemoglobin from a subject, the method comprising:
    introducing the test sample into a first and a second reaction cell, each reaction cell comprising a primary electrode and a reference electrode;
    adding hydrogen peroxide to the reaction cells;
    measuring a first current generated between the primary electrode and the reference electrode in each reaction cell;
    adding inositol hexaphosphate to the first reaction cell and 2,3-diphosphoglycerate to the second reaction cell; and
    measuring a second current generated between the primary electrode and the reference electrode in each reaction cell,
    wherein the absence of a change between the first current and the second current in each reaction cell indicates a diagnosis of malaria in the subject.

17. The method of claim 16, wherein (i) an increase between the measured first current and the second current in the first reaction cell; (ii) a decrease between the measured first current and the second current in the second reaction cell; or (iii) both (i) and (ii) indicates that the subject does not have malaria.

18. The method of claim 16, wherein the inositol hexaphosphate is added to the reaction cell at a final concentration from about 50 to about 250 μM.

19. The method of claim 16, wherein the 2,3-diphosphoglycerate is added to the reaction cell at a final concentration from about 1 to about 3 mM.

* * * * *

UNITED STATES PATENT AND TRADEMARK OFFICE
CERTIFICATE OF CORRECTION

| | |
|---|---|
| PATENT NO. | : 8,287,719 B2 |
| APPLICATION NO. | : 12/750304 |
| DATED | : October 16, 2012 |
| INVENTOR(S) | : Bhattacharya |

It is certified that error appears in the above-identified patent and that said Letters Patent is hereby corrected as shown below:

Delete Title Page and attach the enclosed Title Page, therefor.

On the Title Page, in Field (56), under "OTHER PUBLICATIONS", in Column 2, Line 5, delete "Vijayaraghava"Highly" and insert -- Vijayaraghava, "Highly --, therefor.

On the Title Page, in Field (56), under "OTHER PUBLICATIONS", in Column 2, Line 10, delete "Kanaori" and insert -- Kanaori, --, therefor.

On the Title Page, in Field (56), under "OTHER PUBLICATIONS", in Column 2, Line 15, delete "Javed A" and insert -- Javed A, --, therefor.

In Fig. 7, Sheet 7 of 8, in Box 4, in Line 3, delete "Healthy Controls" and insert -- Healthy Controls. --, therefor.

Delete sheet 7 and substitute the attached sheet containing Fig. 7, therefor.

In Column 3, Line 60, delete "an graph" and insert -- a graph --, therefor.

In Column 3, Line 65, delete "an graph" and insert -- a graph --, therefor.

In Column 4, Line 4, delete "an graph" and insert -- a graph --, therefor.

In Column 4, Line 59, delete "two a" and insert -- two α --, therefor.

In Column 5, Line 30, delete "the is" and insert -- is --, therefor.

In Column 7, Line 3, delete "a electrocatalytic" and insert -- an electrocatalytic --, therefor.

Signed and Sealed this
Nineteenth Day of February, 2013

Teresa Stanek Rea
*Acting Director of the United States Patent and Trademark Office*

(12) United States Patent
Bhattacharya

(10) Patent No.: US 8,287,719 B2
(45) Date of Patent: Oct. 16, 2012

(54) METHODS FOR THE DETECTION AND DIAGNOSIS OF MALARIA USING AN ELECTROCHEMICAL SENSOR

(75) Inventor: Jaydeep Bhattacharya, Kolkata (IN)

(73) Assignee: Empire Technology Development LLC, Wilmington, DE (US)

( * ) Notice: Subject to any disclaimer, the term of this patent is extended or adjusted under 35 U.S.C. 154(b) by 318 days.

(21) Appl. No.: 12/750,304

(22) Filed: Mar. 30, 2010

(65) Prior Publication Data

US 2011/0192731 A1 Aug. 11, 2011

(30) Foreign Application Priority Data

Feb. 9, 2010 (IN) ............................ 118/KOL/2010

(51) Int. Cl.
*G01F 1/64* (2006.01)
*G01N 27/26* (2006.01)
*G01N 17/00* (2006.01)

(52) U.S. Cl. .................. 205/792; 205/777.5; 436/66

(58) Field of Classification Search .................. 205/792; 204/777.5, 403.01; 436/66
See application file for complete search history.

(56) References Cited

U.S. PATENT DOCUMENTS

2004/0099531 A1 5/2004 Srinivasan et al.

OTHER PUBLICATIONS

Abdollah Salimi, Ensiyeh Sharifi, Abdollah Noorbakhsh, Saied Soltanian, Direct voltammetry and electrocatalytic properties of hemoglobin immobilized on a glassy carbon electrode modified with nickel oxide nanoparticles, Electrochemistry Communications, vol. 8, Issue 9, Sep. 2006, pp. 1499-1508.*

Kit Mukesh K. Sharma, Vepa K. Rao, Gauri S. Agarwal, Ganga P. Rai, N. Gopalan, Shri Prakash, S. K. Sharma, and R. Vijayaraghava "Highly Sensitive Amperometric Immunosensor for Detection of *Plasmodium falciparum* Histidine-Rich Protein 2 in Serum of Humans with Malaria: Comparison with a Commercial" J. Clin. Microbiol. Nov. 2008 46:11 3759-3765.*

Takashi Yonetani, Sungick Park, Antonio Tsuneshige, Kiyohiro Imai, and Kenji Kanaori "Global Allostery Model of Hemoglobin: Modulation of O2 Affinity, Cooperativity, and Bohr Effect by Heterotropic Allosteric Effectors" J. Biol. Chem. 2002 277: 34508-34520. First Published on Jul. 9, 2002.*

Rezaei-Zarchi S, Saboury A A, Ghourchian H, Hong J, Barzegar A, Norouzi P, Moosavi-Movahedi A A, Ganjali M R and Javed A "Electrochemical investigation of the effect of some organic phosphates on haemoglobin"; J. Biosci. 32 271-278, 2007.*

"Malaria: Parasite Biology, Pathogenesis, and Protection," Sherman, I. W., Ed.; ASM Press, Washington D.C., 1998.

Atha, D. et al., "Tetramer-Dimer Dissociation in Hemoglobin and the Bohr Effect," *The Journal of Biological Chemistry*, vol. 251, No. 18, Sep. 25, 1976, pp. 5537-5543.

Bunn, H. F., "Differences in the Interaction of 2,3-Diphosphoglycerate with Certain Mammalian Hemoglobins," *Science*, vol. 172, Jun. 4, 1971, pp. 1049-1050.

(Continued)

*Primary Examiner* — Jeffrey T Barton
*Assistant Examiner* — Louis Rufo
(74) *Attorney, Agent, or Firm* — Foley & Lardner LLP

(57) ABSTRACT

Disclosed are apparatuses for detecting hemoglobin in patient samples. The apparatuses include a primary electrode and a reference electrode. The apparatus is configured to measure current or voltage generated between the primary electrode and the reference electrode in response a redox reaction catalyzed by hemoglobin. The apparatuses can detect a variety of hemoglobins, including dimeric hemoglobin associated with malaria. Also disclosed are biosensor systems including the apparatuses and methods of using the biosensor systems.

19 Claims, 8 Drawing Sheets

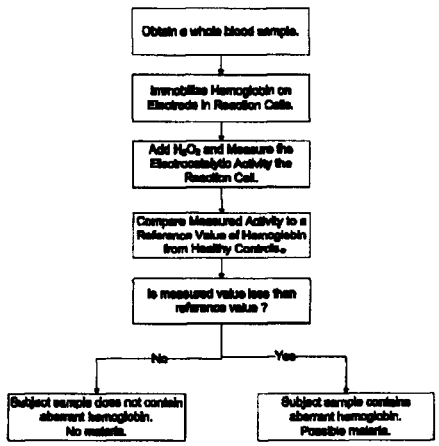

UNITED STATES PATENT AND TRADEMARK OFFICE
CERTIFICATE OF CORRECTION

PATENT NO. : 8,287,719 B2
APPLICATION NO. : 12/750304
DATED : October 16, 2012
INVENTOR(S) : Bhattacharya Page 1 of 4

It is certified that error appears in the above-identified patent and that said Letters Patent is hereby corrected as shown below:

Delete Title Page and attach the enclosed Title Page, therefor.

On the Title Page, in Field (56), under "OTHER PUBLICATIONS", in Column 1, Line 2, delete "Direct" and insert -- "Direct --, therefor.

On the Title Page, in Field (56), under "OTHER PUBLICATIONS", in Column 2, Line 5, delete "Vijayaraghava"Highly" and insert -- Vijayaraghava, "Highly --, therefor.

On the Title Page, in Field (56), under "OTHER PUBLICATIONS", in Column 2, Line 10, delete "Kanaori" and insert -- Kanaori, --, therefor.

On the Title Page, in Field (56), under "OTHER PUBLICATIONS", in Column 2, Line 15, delete "Javed A" and insert -- Javed A, --, therefor.

In Fig. 7, Sheet 7 of 8, in Box 4, in Line 3, delete "Healthy Controls" and insert -- Healthy Controls. --, therefor.

Delete sheet 7 and substitute the attached sheet containing Fig. 7, therefor.

In Column 3, Line 60, delete "an graph" and insert -- a graph --, therefor.

In Column 3, Line 65, delete "an graph" and insert -- a graph --, therefor.

In Column 4, Line 4, delete "an graph" and insert -- a graph --, therefor.

In Column 4, Line 59, delete "two a" and insert -- two α --, therefor.

This certificate supersedes the Certificate of Correction issued February 19, 2013.

Signed and Sealed this
Nineteenth Day of March, 2013

Teresa Stanek Rea
*Acting Director of the United States Patent and Trademark Office*

In Column 5, Line 30, delete "the is" and insert -- is --, therefor.

In Column 7, Line 3, delete "a electrocatalytic" and insert -- an electrocatalytic --, therefor.

(12) United States Patent
Bhattacharya

(10) Patent No.: US 8,287,719 B2
(45) Date of Patent: Oct. 16, 2012

(54) METHODS FOR THE DETECTION AND DIAGNOSIS OF MALARIA USING AN ELECTROCHEMICAL SENSOR

(75) Inventor: Jaydeep Bhattacharya, Kolkata (IN)

(73) Assignee: Empire Technology Development LLC, Wilmington, DE (US)

( * ) Notice: Subject to any disclaimer, the term of this patent is extended or adjusted under 35 U.S.C. 154(b) by 318 days.

(21) Appl. No.: 12/750,304

(22) Filed: Mar. 30, 2010

(65) Prior Publication Data

US 2011/0192731 A1    Aug. 11, 2011

(30) Foreign Application Priority Data

Feb. 9, 2010    (IN) .............................. 118/KOL/2010

(51) Int. Cl.
*G01F 1/64* (2006.01)
*G01N 27/26* (2006.01)
*G01N 17/00* (2006.01)

(52) U.S. Cl. ......................... 205/792; 205/777.5; 436/66

(58) Field of Classification Search .................. 205/792; 204/777.5, 403.01; 436/66
See application file for complete search history.

(56) References Cited

U.S. PATENT DOCUMENTS

2004/0099531 A1    5/2004    Srinivasan et al.

OTHER PUBLICATIONS

Abdollah Salimi, Ensiyeh Sharifi, Abdollah Noorbakhsh, Saied Soltanian, Direct voltammetry and electrocatalytic properties of hemoglobin immobilized on a glassy carbon electrode modified with nickel oxide nanoparticles, Electrochemistry Communications, vol. 8, Issue 9, Sep. 2006, pp. 1499-1508.*

Kit Mukesh K. Sharma, Vepa K. Rao, Gauri S. Agarwal, Ganga P. Rai, N. Gopalan, Shri Prakash, S. K. Sharma, and R. Vijayaraghava"Highly Sensitive Amperometric Immunosensor for Detection of *Plasmodium falciparum* Histidine-Rich Protein 2 in Serum of Humans with Malaria: Comparison with a Commercial" J. Clin. Microbiol. Nov. 2008 46:11 3759-3765.*

Takashi Yonetani, Sunglck Park, Antonio Tsuneshige, Kiyohiro Imai, and Kenji Kanaori "Global Allostery Model of Hemoglobin: Modulation of O2 Affinity, Cooperativity, and Bohr Effect by Heterotropic Allosteric Effectors" J. Biol. Chem. 2002 277: 34508-34520. First Published on Jul. 9, 2002.*

Rezaei-Zarchi S, Saboury A A, Ghourchian H, Hong J, Barzegar A, Norouzi P, Moosavi-Movahedi A A, Ganjali M R and Javed A "Electrochemical investigation of the effect of some organic phosphates on haemoglobin"; J. Biosci. 32 271-278, 2007.*

"Malaria: Parasite Biology, Pathogenesis, and Protection," Sherman, I. W., Ed.; ASM Press, Washington D.C., 1998.

Atha, D. et al., "Tetramer-Dimer Dissociation in Hemoglobin and the Bohr Effect," *The Journal of Biological Chemistry*, vol. 251, No. 18, Sep. 25, 1976, pp. 5537-5543.

Bunn, H. F., "Differences in the Interaction of 2,3-Diphosphoglycerate with Certain Mammalian Hemoglobins," *Science*, vol. 172, Jun. 4, 1971, pp. 1049-1050.

(Continued)

*Primary Examiner* — Jeffrey T Barton
*Assistant Examiner* — Louis Rufo
(74) *Attorney, Agent, or Firm* — Foley & Lardner LLP

(57) ABSTRACT

Disclosed are apparatuses for detecting hemoglobin in patient samples. The apparatuses include a primary electrode and a reference electrode. The apparatus is configured to measure current or voltage generated between the primary electrode and the reference electrode in response a redox reaction catalyzed by hemoglobin. The apparatuses can detect a variety of hemoglobins, including dimeric hemoglobin associated with malaria. Also disclosed are biosensor systems including the apparatuses and methods of using the biosensor systems.

19 Claims, 8 Drawing Sheets